United States Patent
Fisher et al.

(10) Patent No.: US 6,362,328 B1
(45) Date of Patent: *Mar. 26, 2002

(54) ASSAYS AND PROBES WITH ENZYME LABELS

(75) Inventors: Mark Fisher, London; Christopher John Taylorson, Ilford; Stuart Harbron, Berkhamsted, all of (GB)

(73) Assignee: London Biotechnology Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,257

(22) PCT Filed: Oct. 29, 1997

(86) PCT No.: PCT/GB97/02981

§ 371 Date: Sep. 20, 1999

§ 102(e) Date: Sep. 20, 1999

(87) PCT Pub. No.: WO98/19168

PCT Pub. Date: May 7, 1998

(30) Foreign Application Priority Data

Oct. 29, 1996 (GB) .............................................. 9622524

(51) Int. Cl.[7] .......................... C07H 21/04; C12Q 1/68; G01N 31/21; G01N 33/53; A61K 39/395
(52) U.S. Cl. .......................... 536/24.3; 435/6; 435/7.1; 435/7.94; 435/188; 422/61; 424/178.1; 424/179.1
(58) Field of Search .......................... 435/6, 7.94, 188, 435/7.1; 536/243; 424/178.1, 179.1; 422/61

(56) References Cited

U.S. PATENT DOCUMENTS

| 4,837,167 A | * | 6/1989 | Schoemaker et al. ....... 436/513 |
|---|---|---|---|
| 5,006,472 A | | 4/1991 | Dove et al. ................... 435/270 |
| 5,145,780 A | | 9/1992 | Oishi et al. ................... 435/262 |
| 5,445,942 A | | 8/1995 | Rabin et al. .................... 435/18 |
| 5,563,063 A | | 10/1996 | Hirasawa et al. ......... 435/252.1 |

FOREIGN PATENT DOCUMENTS

| DE | 2156518 | * 10/1985 | .......... G01N/33/53 |
|---|---|---|---|
| EP | 0061071 | 9/1982 | .......... G01N/33/54 |
| EP | 0124124 | 11/1984 | .......... G01N/33/54 |
| EP | 0401001 | 12/1990 | ......... C07D/321/00 |
| EP | 0516948 | 12/1992 | .......... G01N/21/76 |
| GB | 2018986 | 10/1979 | .......... G01N/33/16 |
| WO | WO90/00252 | 1/1990 | .......... G01N/33/58 |
| WO | WO96/41015 | 12/1996 | .......... G01N/33/58 |

OTHER PUBLICATIONS

Sigma catalog, 1994, p. 754.*

Harbon et al, Amplified Assay of Alkaline Phosphatase Using Flavinadenine Dinucleotide Phosphate as Substrate (1992)Anal. Biochem. 206: 119–124.

Barber and Westermann, The rodlet of Semotilus atromaculatus and Catostomus commersoni(Teleostei): studies on its identity using histochemistry and Dnase I —gold, Rnase A–gold and S1 nuclease–gold labeling techniques(1986) Can J Zool 64: 805–13.

Fujimoto et al, Substrate Specificity of Nuclease $P_1$ (1974) Agr. Biol. Chem. 38(9): 1555–1561.

* cited by examiner

Primary Examiner—W. Gary Jones
Assistant Examiner—B J Forman
(74) Attorney, Agent, or Firm—Law Office of Luann Cserr

(57) ABSTRACT

Probes comprise S1 and P1 nuclease (as an enzyme label) linked to a specific binding member such as a nucleotide sequence or an antibody. Such probes are useful for sandwich assays. As compared with known probes using alkaline phosphatase as a label, advantages include relative insensitivity to phosphate and elevated temperature and reduced risk of nonspecific binding.

10 Claims, 5 Drawing Sheets

ASSAYS AND PROBES WITH ENZYME LABELS

This application is a 371 of PCT/GB97/02981, filed Oct. 29, 1997.

TECHNICAL FIELD

This invention relates to probes comprising enzyme labels and specific binding members such as antibodies and single-stranded nucleic acids, and assays employing such probes.

BACKGROUND ART

The use of enzymes as labels in a wide variety of clinical, veterinary and environmental diagnostic assays including enzyme immunoassays and nucleic acid probe-based assays is well known. One example of the use of these employs a sandwich format in which an immobilized antibody, antigen or nucleic acid is used to recognize and bind to a portion of the molecule to be detected. An appropriate enzyme-labelled antibody or nucleic acid probe is then introduced which binds to a different portion of the complex to be measured. This results in the formation of a complex immobilized to the solid surface which is labelled with the enzyme. After several washing steps to remove all traces of the original sample and the excess unbound labelled moiety, a substrate for the enzyme is introduced, and the presence of the enzyme detected by its action on a substrate to produce a change in colour, fluorescence, redox state, or to produce light.

It is important that enzymes employed as labels catalyze a reaction which has an easily detectable product, and have a high turnover number to allow sensitive detection: horseradish peroxidase and alkaline phosphatase are most common. Although sensitive chemiluminometric assays for horseradish peroxidase have been described which allow small amounts of enzyme to be detected, problems associated with its use include lack of enzyme and substrate stability and the presence of endogenous peroxidases in samples.

For alkaline phosphatase, enzyme amplification cycles have been described which further reduce the amount of enzyme which can be detected, thereby extending the detection limit. For example, in U.S. Pat. No. 5,445,942 to Rabin et al., entitled "Amplification Assay for hydrolase enzymes", a method is described for detecting a hydrolase enzyme able to hydrolyze a synthetic derivative of FAD substituted in such a way that it yields FAD when hydrolyzed. The FAD produced forms an active holoenzyme from the corresponding apoenzyme. This approach allows the detection of small amounts of alkaline phosphatase in short periods of time. For example, we have used such an amplification system in which the apoenzyme is apo-D-amino acid oxidase to measure 0.1 amol of alkaline phosphatase in less than 30 minutes (Harbron S, et al., Anal. Biochem. (1992) 206: 119–124).

However, the use of alkaline phosphatase as the label enzyme has a number of shortcomings: its large size (MW= 140,000) means that it can sterically hamper the association of the antibody or nucleic acid probe with its target; its nature as a membrane-associated protein means that it binds non-specifically to many surfaces; it is very sensitive to the presence of phosphate carried over from previous assay stages; it has limited stability at the temperatures often used in nucleic acid hybridization steps; and it is a commonly occurring enzyme in many tissues and occurs in the environment at large as a component of bacteria and other microorganisms. Rabin et al. describe the use of the amplification assay for the detection of sulphatases, carboxylesterases, acetylesterase and venom phosphodiesterase which may obviate some of these problems, but they do not teach that the approach could be used for the assay of enzymes of the nuclease class, such as nuclease S1 and nucleate P1. It is known that nuclease P1 hydrolyses Coenzyme A (Fujimoto et al., Agr. Biol, Chem. (1974) 38: 1555–1561).

EP-A-401,001 concerns novel dioxetanes having a substituent -X-Y-Z where Z and Y are protecting groups which are removable successively, leading to chemiluminescence. For a sandwich assay, Z may be removed by a first triggering enzyme E1 which is directly or indirectly bound to an antigen, antibody or nucleic acid probe. E1 may be a nuclease.

Further examples of assays involving enzyme-containing probes are provided by EP-A-0,304,934, U.S. Pat. No. 5,563,063, WO-A-96/41015, WO-A-90/00252, EP-A-0, 061,071, EP-A-0,124,124, EP-A-0,516,948 and GB-A-2018986.

DISCLOUSRE OF INVENTION

We have discovered that both nuclease S1 and nuclease P1 can hydrolyze the synthetic analogue of FAD in which the 3' hydroxyl group on the ribose moiety of FAD is esterified with phosphoric acid to give 3' FADP, thereby giving a new means of assaying these enzymes in an extremely rapid and sensitive fashion. But Fujimoto et al. also showed that nuclease P1 hydrolyses single stranded DNA and RNA, which would indicate that this enzyme is unsuitable for labelling nucleic acid probes. In fact, the prior art teaches that nucleases are used for degrading nucleic acids: thus U.S. Pat. No. 5,145,780, to Oishi and Aoi describes an enzyme preparation produced by a fungus such as Trichoderma, Aspergillus and Fusarium which contains a nuclease that is active even after heating at 100° C. for 30 minutes. This enzyme preparation may be effectively used when it is necessary to decompose nucleic acids at elevated temperature over a prolonged period. U.S. Pat. No. 5,006, 472, to Dove and Mitra, discloses a method for purifying rDNA or monoclonal antibody culture products by using nuclease enzyme treatment to degrade undesirable residual nucleic acids to a molecular size or charge range sufficiently different from the product to be purified so that this difference can be exploited in a subsequent purification step (e.g. precipitation, size exclusion chromatography or ion exchange chromatography).

Although it would not therefore be expected that nuclease P1 and nuclease S1 could be used to label nucleic acids, Fujimoto et al. demonstrated that the ability of nuclease P1 to hydrolyze single-stranded nucleic acids was pH dependent, and we have found that pH values greater than 7.0 allow the labelling of nucleic acids with these nucleases.

Broadly, the present invention relates to the use of P1 and S1 nucleases as enzyme labels for assays. Thus in one aspect the invention provides a probe which comprises a nuclease (particularly P1 or S1) coupled to a specific binding member ("sbm") (generally an antibody or a single-stranded nucleic acid). The nuclease is preferably covalently attached to the sbm.

In another aspect the invention provides a method of producing a probe which comprises coupling a nuclease to an sbm.

In further aspects the invention provides an assay method employing a probe according to the first aspect, and a kit for carrying out such an assay.

A preferred type of sbm is antibodies (particular IgG antibodies) and functional fragments thereof capable of binding to a target in an assay procedure.

Another preferred type of sbm is nucleic acids (DNA, RNA or analogues thereof), generally oligonucleotides. The nucleic acid may be produced with a derivatised 5'-end (e.g. trityl-hexyl thiol derivatised) to facilitate coupling to a nuclease which has been rendered susceptible to disulphide exchange, e.g. being 2-pyridyl disulphide activated.

Preferred embodiments of the invention may enable one to achieve one or more of the following objects and advantages:

(a) to provide an enzyme label which is small and which does not interfere with the association of antibody and antigen, nor of complementary strands of nucleic acid;

(b) to provide an enzyme label which may be easily conjugated to antibodies and nucleic acids using well-known methodologies;

(c) to provide an enzyme label which is not membrane associated in its natural state, and which is secreted into the growth medium, and which therefore has a low level of non-specific binding to solid surfaces;

(d) to provide an enzyme label which is largely insensitive to the presence of phosphate, allowing it to be used in automated assay machinery in which phosphate-containing washing solutions are routinely used;

(e) to provide an enzyme label which has good temperature stability, allowing it to be used at high temperature, particularly in nucleic acid assays;

(f) to provide an enzyme label which is not a commonly occurring enzyme, thereby avoiding contamination from endogenous enzyme in the sample.

Further objects and advantages are to provide the use as enzyme labels of enzymes which are commercially available, which are not inhibited by phosphate monoesters which may be included in the assay solution to prevent endogenously occurring phosphatases from hydrolysing 3' FADP, which do not hydrolyze single-stranded nucleic acids at the pH employed in the assay solution, and which can be assayed using an enzyme amplification system.

Some embodiments of the invention will be described in more detail, by way of example, with reference to the accompanying drawings.

MODES FOR CARRYING OUT THE INVENTION

Figure 1:
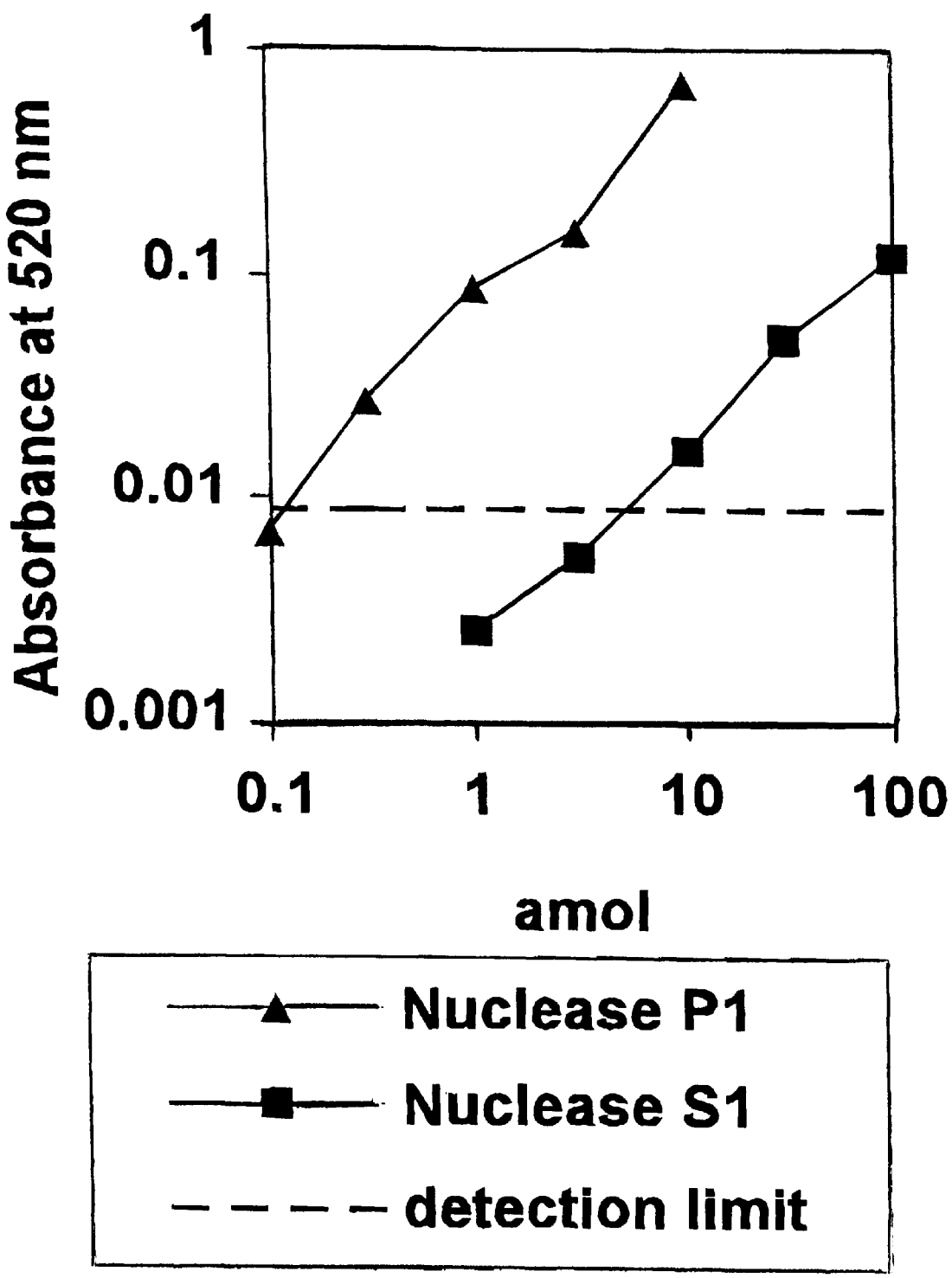
FIG. 1 shows a standard curve for the 3'FADP-based enzyme amplification assay of nuclease P1 and S1.

One preferred type of embodiment of the present invention employs the enzyme nuclease P1 covalently attached to an antibody. The covalent attachment may be achieved by a number of well-known methods using a wide range of heterobifunctional reagents. For example, the method of Carlsson et al. (*Biochem J* (1978) 173: 723–737) may be used: nuclease P1 is reacted with 3-[(2)-pyridyldithio] propionic acid N-hydroxysuccinimide ester (SPDP) to give a 2-pyridyl disulphide-activated enzyme. This is mixed with an IgG antibody, and a disulphide exchange reaction yields a nuclease P1-IgG antibody conjugate.

This conjugate may, for example, be used in a sandwich immunoassay in which an antibody immobilized on a microtitre plate binds a target antigen from a sample, and the nuclease P1-IgG antibody conjugate binds to another site on the antigen, producing an Immobilized complex labelled with nuclease P1. Following a number of washing steps nuclease P1 which has become immobilized in this way can be detected using the prosthetogenic amplification system of Rabin et al. For this assay, a solution containing buffer, 3'FADP, apoglucose oxidase, glucose, horseradish peroxidase and its substrates are added. 3'FADP is hydrolyzed by nuclease P1 to yield FAD which is bound by apoglucose oxidase. The hologlucose oxidase thus formed oxidizes glucose to produce hydrogen peroxide, which is in turn a substrate for horseradish peroxidase, yielding a coloured product conveniently quantitated in a microplate reader. To eliminate signal caused by endogenous phosphatase remaining after the washing step, which would also hydrolyze 3'FADP to give FAD, a phosphatase substrate such as p-nitrophenyl phosphate or 2-glycerophosphate, may be added. The phosphatase contaminant will hydrolyze this in preference to 3'FADP.

Another preferred type of embodiment of the present invention employs the enzyme nuclease P1 covalently attached to a nucleic acid. The nucleic acid may be DNA or RNA or an analogue thereof. The nucleic acid may be an oligonucleotide produced by solid-phase chemistry by a Nucleic Acid synthesizer having a trityl-hexyl thiol derivatized 5'-end. This allows disulphide exchange with the 2-pyridyl disulphide-activated enzyme described above to yield a nuclease P1-oligonucleotide conjugate.

This conjugate may, for example, be used in a sandwich hybridization assay in which an oligonucleotide immobilized on a microtitre plate binds a single-stranded target nucleic acid from a sample denatured with alkali. After annealing and neutralisation of the alkali, the nuclease P1-oligonucleotide conjugate binds to another site on the target nucleic acid, producing an immobilized complex labelled with nuclease P1. Following a number of washing steps nuclease Pi which has become immobilized in this way can be detected using the prosthetogenic amplification system of Rabin et al. For this assay, a solution containing buffer, 3'FADP, apoglucose oxidase, glucose, horseradish peroxidase and its substrates are added. 3'FADP is hydrolyzed by nuclease P1 to yield FAD which is bound by apoglucose oxidase. The hologlucose oxidase thus formed oxidizes glucose to produce hydrogen peroxide, which is in turn a substrate for horseradish peroxidase, yielding a coloured product conveniently quantitated in a microplate reader. To eliminate signal caused by endogenous phosphatase remaining after the washing step, which would also hydrolyze 3'FADP to give FAD, a phosphatase substrate such as p-nitrophenyl phosphate or 2-glycerophosphate, may be added, The phosphatase contaminant will hydrolyze this in preference to 3'FADP.

EXAMPLE 1

Standardization of Nuclease P1

Nuclease P1 (1 mg; obtained from Sigma Chemical Company, batch no: 107F0799) was dissolved in 1 ml of water to give a concentration of 22.7 $\mu$M and stored at 4° C. The activity of this solution was assayed in the following mixture: 0.16 mM NADH, 1 mM ATP, 1 mM PEP, 1 mM $MgSO_4$, 20 mM KCl, 0.5 mM adenosine 3',5'-bisphosphate, 1 U pyruvate kinase, 1 U lactate dehydrogenase and 1 U myokinase in 50 mM HEPES buffer, pH 7.2, in a total volume of 1 ml. From the change in absorbance at 340 nm the activity of nuclease P1 was solution was found to be 320 U/ml, assuming a molar extinction coefficient of 6220 for NADH.

EXAMPLE 2

Amplification Assay of Nuclease P1 and Nuclease S1

A solution of nuclease P1 standardized according to Example 1 was serially diluted in 50 mM citrate buffer adjusted to pH 6.5 with NaOH. The assay mixture contained 20 $\mu$M 3'FADP, 0.1 mM 4-aminoantipyrine, 2 mM DHSA, 1 $\mu$g horseradish peroxidase, 0.1 M glucose and 0.1 $\mu$M apoglucose oxidase in a total volume of 0.1 ml. The change in absorbance was monitored at 520 nm in a Dynatech MR7000 plate reader fitted with a thermostatically controlled plate holder set to 25° C. FIG. 1 shows the performance of the nuclease P1 assay. After a 15 minute assay period, the detection limit (defined as 3 times the standard deviation of the background reading) was 0.2 amol. Nuclease S1 was assayed in a similar manner, and the detection limit was 4 amol (FIG. 1).

EXAMPLE 3

Effect of Phosphate on the Activity of Nuclease P1 and Alkaline Phosphatase

Figure 2:
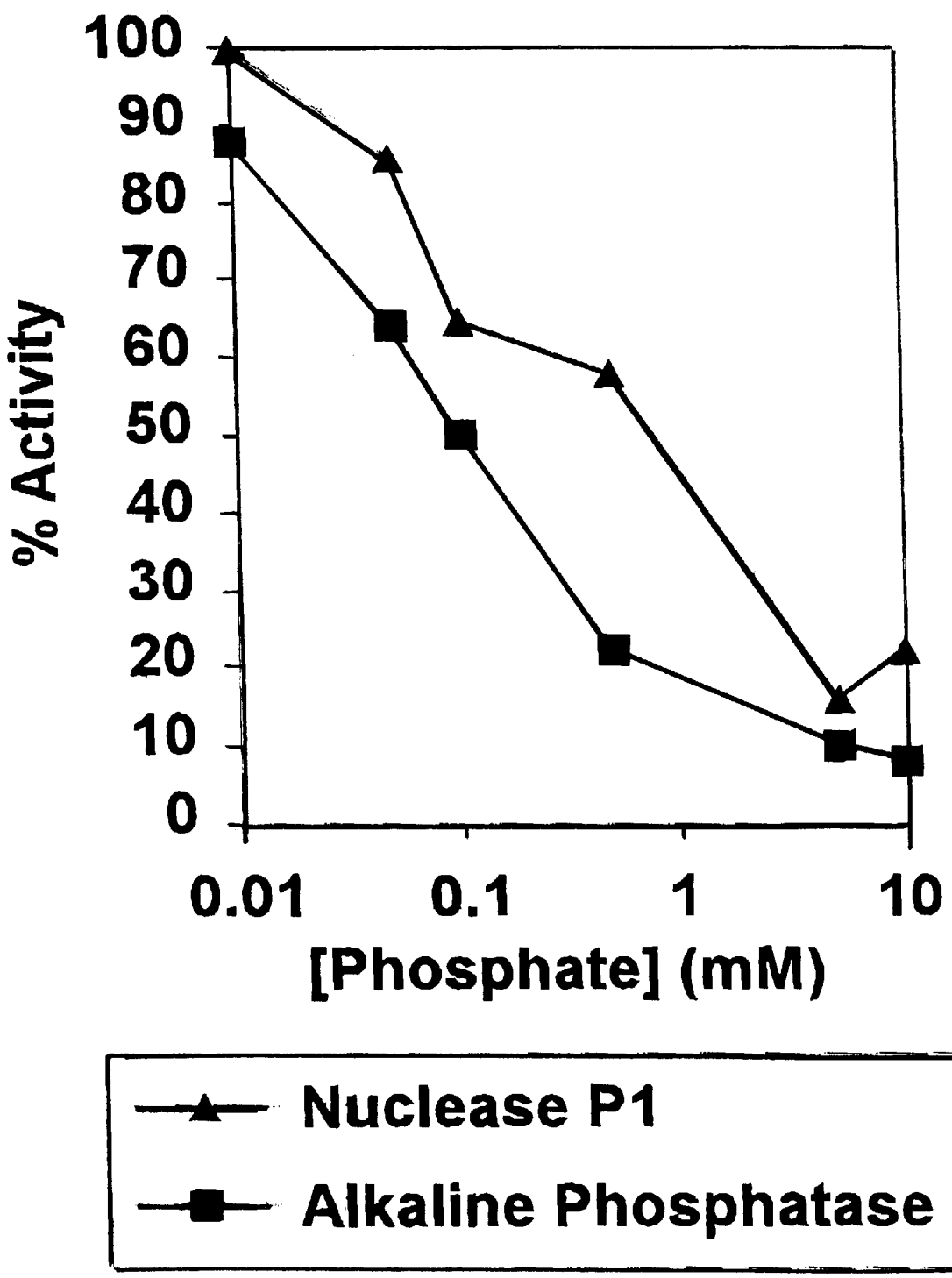
FIG. 2 is a graphic comparison of the effect of phosphate on the 3'FADP-based enzyme amplification assay of alkaline phosphatase and nuclease P1.

Phosphate buffer, pH 6.5, was added to the reaction mixture described in Example 2 to give a final concentration of phosphate ranging from 0 to 10 mM. The effect of phosphate on the activity of nuclease P1 is shown in FIG. 2. This was compared with the effect of phosphate on alkaline phosphatase. The same assay mixture was used, but 0.1 M Tris buffer, adjusted to pH 8.9 with HCl was used instead of the citrate buffer, and the phosphate buffer which was added was also adjusted to pH 8.9. Clearly, phosphate has less of an effect on nuclease P1 than on alkaline phosphatase.

EXAMPLE 4

Effect of p-Nitrophenyl Phosphate on the Activity of Nuclease P1

Figure 3:
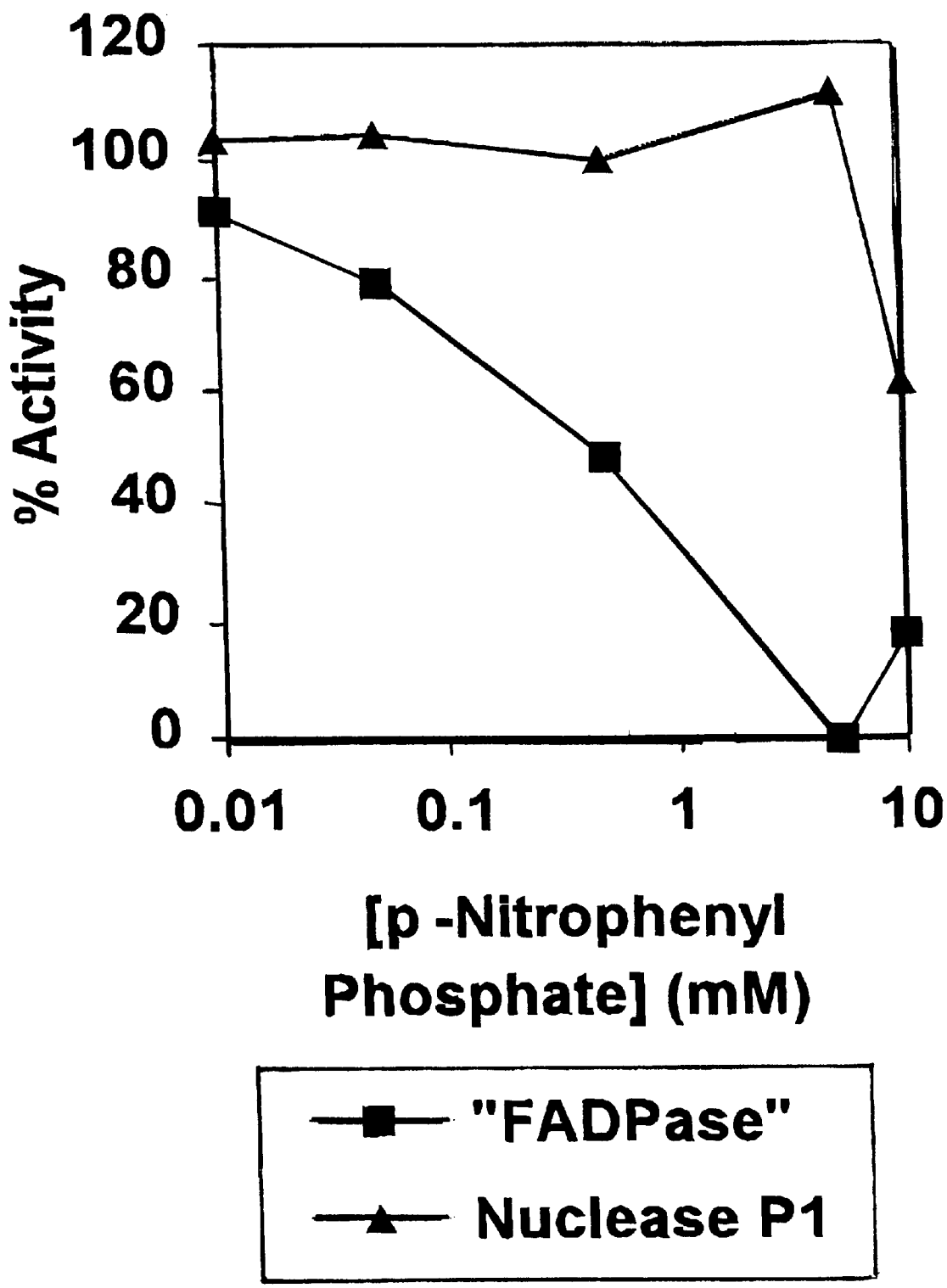
FIG. 3 is a graphic comparison of the effect of p-nitrophenyl phosphate on the activity of nuclease P1 and endogenous phosphatase ("FADPase") activity measured using the 3'FADP-based enzyme amplification assay.

The effect of p-nitrophenyl phosphate on the activity of nuclease P1 was investigated by adding p-nitrophenyl phosphate to the assay mixture described in Example 2, to give a final concentration ranging between 0 and 10 mM. The effect of the added p-nitrophenyl phosphate on the background color generation in the absence of nuclease P1 was also noted. This background is due to endogenous "FADPase" in the apoglucose oxidase used in the assay. At concentrations up to approximately 5 mM, added p-nitrophenyl phosphate has no effect on nuclease P1, but reduces the background signal by 80–100% (FIG. 3).

EXAMPLE 5

Oligonucleotide Synthesis

Oligonucleotide were synthesized on a Cyclone™ DNA synthesizer using the Expedite™ chemistry. The DNA to be immobilized on a microtitre plate, known as the capture DNA probe, was designed to capture a plasmid containing the 5'-end of the gene encoding human pancreatic ribonuclease, including the bovine leader sequence (see Taylorson et al. WO96/2001). This plasmid also had R4A, K6E and K66E mutations. The sequence was:
5'-GAATTCCCATGGCGAAGGAATCCGCTGCCGCT AAA-3' (SEQ ID NO: 1).

The DNA to be labelled with nuclease P1, known as the reporter probe, was complimentary to a region in the middle of the ribonuclease gene containing the K66E mutation. This probe was derivatized at the 5' end with a trityl-hexyl thiol group to facilitate linkage to nuclease P1. The sequence was:
5'-GGTCACCTGCGAAAACGGGCAGG-3' (SEQ ID NO: 2).

The oligonucleotide were freeze-dried and stored at 4° C. until required.

EXAMPLE 6

Derivatization of Nuclease P1

Nuclease P1 (5 mg) was dissolved in 0.5 ml 0.1 M sodium bicarbonate pH 7.5 containing 0.1 M sodium chloride and desalted by gel filtration on Sephadex G25 (NAP-5 column, Pharmacia) equilibrated with the same buffer. This enzyme solution was incubated with a 50-fold molar excess of 3-(2)-pyridyldithio)-propionic acid N-hydroxysuccinimide ester (SPDP) at room temperature for 30 minutes, Unreacted SPDP was removed by gel filtration On Sephadex G25 (NAP 10 column, Pharmacia) equilibrated with the bicarbonate buffer. The 2-pyridyl disulphide-activated nuclease P1 was stored at 4° C.

EXAMPLE 7

Conjugation of Nuclease P1 to Antihuman IgG

The 2-pyridyl disulphide-activated nuclease P1 prepared according to Example 6 was transferred to 0.1 M sodium acetate buffer, pH 4.5, containing 0.1 M sodium chloride by gel filtration on Sephadex G 25. Antihuman IgG ($\gamma$-chain specific) was dissolved in the acetate buffer to give a concentration of 3 mg/ml, and desalted by gel filtration on Sephadex G 25 (NAP 5 column, Pharmacia) equilibrated with the same buffer. Activated nuclease P1 was mixed with the IgG solution at a molar ratio of 3:1, and incubated at room temperature for 45 minutes, and then at 4° C. for a further 16 hours. The conjugate was transferred to 20 mM bis-Tris buffer, pH 6.5, containing 1 mM CHAPS by chromatography on Sephadex G25 equilibrated with the same buffer, prior to purification by ion exchange chromatography on a Pharmacia Mono-Q column. The conjugate was eluted in the same buffer containing 20 mM sodium chloride.

EXAMPLE 8

Conjugation of Nuclease P1 to an Oligonucleotide

Nuclease P1 was linked to 2-pyridyl disulphide as described in Example 6 and stored in 0.1 M sodium bicarbonate, pH 7.5, containing 0.1 M sodium chloride at 4°

C. The reporter oligonucleotide of Example 5 was dissolved in 0.5 ml 0.1 M sodium bicarbonate buffer, pH 7.5, containing 0.1 M sodium chloride to give a final concentration of 0.36 mM. This was incubated with activated nuclease P1 prepared according to Example 6 at a mole ratio of 1:2 at room temperature for 45 minutes, followed by an incubation at 4° C. for 16 h.

The conjugate was transferred to 20 mM bis-Tris propane buffer, pH 7.5, containing 1 mM CHAPS by chromatography on Sephadex G25, and purified by ion-exchange chromatography on a Pharmacia Mono Q column. A sodium chloride gradient in the same buffer was used applied to the column and the conjugate was eluted at a molar concentration of 0.25 M.

EXAMPLE 9

Enzyme Immunoassay Employing Nuclease P1-conjugated Antihuman IgG

Standard solutions containing human serum IgG antibodies to measles were incubated in microtitre plates coated with purified measles antigen (Edmonston strain, obtained from Sigma Chemical Co as the SIA measles IgG assay kit) for 30 min at room temperature. Each well was washed 5 times with a buffered solution containing surfactant (as supplied in the kit from Sigma) . 200 µl of a 2 nM solution of nuclease P1 conjugate in 20 mM bis-Tris buffer, pH 6.5, containing 1 mM CHAPS was added to each well. The plate was covered and incubated at room temperature for 30 minutes. Each well was washed 5 times with the buffered solution containing surfactant to remove excess conjugate. The bound conjugate was quantitated using the amplification assay of Example 2, with an assay time of 5 minutes.

Figure 4:
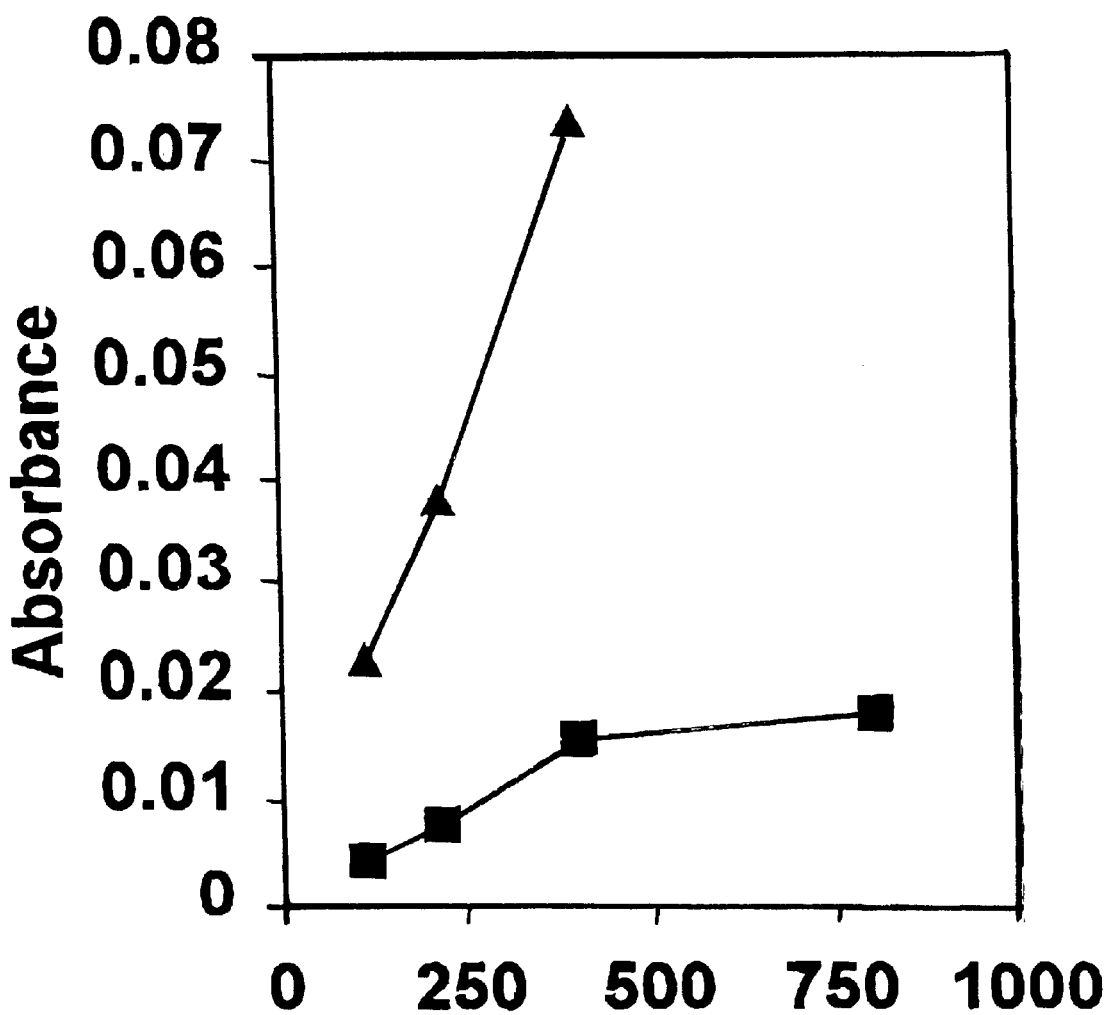
FIG. 4 is a graphic comparison of a nuclease P1-based enzyme immunoassay for measles (using the 3'FADP-based enzyme amplification assay and measuring the absorbance at 520 nm) with an alkaline phosphatase-based enzyme immunoassay, (using p-nitrophenyl-phosphate and measuring the absorbance at 405 nm)

FIG. 4 compares the absorbance produced using the amplification assay for nuclease P1 described in Example 2 with that obtained using an alkaline phosphatase-labeled antibody assayed using p-nitrophenyl phosphate (the method normally used with the SIA measles IgG assay kit). The nuclease P1-based enzyme immunoassay is approximately 5 times more sensitive than the alkaline phosphatase/p-nitrophenyl phosphatase based system of the kit.

EXAMPLE 10

Covalent Attachment of Capture Oligonucleotide to a Microtitre Plate

The capture oligonucleotide of Example 5 was immobilized to the walls of a Covalink NH microtitre plate (Nunc) as described by Rasmussen et al. (*Anal Biochem* (1991) 198: 138–142). The capture oligonucleotide was dissolved in 1 ml sterile water and its concentration determined from its absorbance at 260 nm. It was phosphorylated using T4 polynucleotide kinase in the presence of a 5-fold molar excess of ATP at 37° C. for 30 minutes. The reaction was terminated by heating to 95° C. followed by rapid cooling on ice. The solution of oligonucleotide was diluted with 143 mM 1-methylimidazole, pH 7.0, to give a final concentration of 1.3 µM, and 70 µl of this solution, containing 91 fmol of oligonucleotide, was added to each well of the Covalink NH microtitre plate. This was followed by 30 µl of 1-ethyl-3-(3-dimethylaminopropyl)-carbodiimide, and the plate was sealed and incubated at 50° C. for 5 hours. Reaction solution was then removed from. the wells and the plate was washed 3 times with 0.4 M sodium hydroxide containing 0.25% (w/v) SDS at 50° C., followed by a further 3 washes at room temperature with 10 mM Tris-HCl buffer, pH 8.0, containing 1 mM EDTA. The plates were stored at 4° C. until required.

EXAMPLE 11

Hybridization and Detection of Plasmid DNA 50 pg of XDNA, dissolved in 95 µl sterile water was added to each well of the microtitre plate prepared in Example 10. This served as a control for non-complementary binding. A further 5 µl of a known amount of the plasmid containing the human RNase mutant and 10 µl 1 M sodium hydroxide were added. This mixture was incubated at room temperature for 10 minutes to denature the plasmid before neutralisation with 8 µl of 0.5 M sodium citrate buffer, pH 3.0, containing 2.21 M sodium chloride and 0.1% Tween 20.

50 µl (34 fmol) of the nuclease P1-conjugated reporter probe, prepared according to Example 8, dissolved in 0.1 M Tris-HCl buffer, pH 7.5, containing 7 mM zinc sulphate, 1% (w/v) PVP, 0.1% N-lauroylsarkosine and 150 mM sodium chloride, was added to each well. After hybridization at 40° C. for 1 hour, the wells were washed 6 times with 20 mM Tris-HCl buffer, pH 7.5, containing 7 mM zinc sulphate, 1% (w/v) PVP, 0.1% N-lauroylsarkosine and 150 mM sodium chloride.

Figure 5:
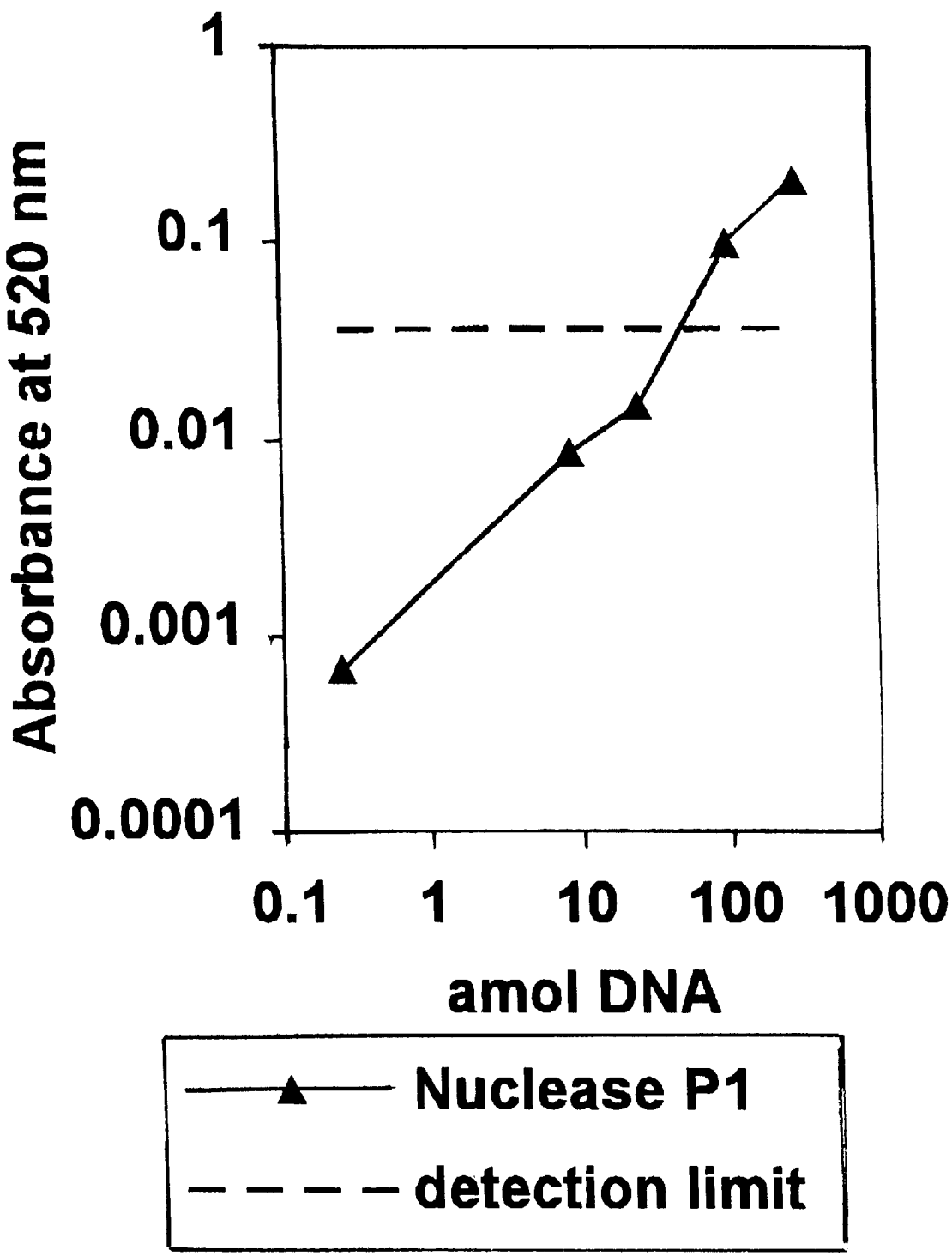
FIG. 5 is a graph showing the results of a microtitre plate-based gene probe assay using a nuclease P1-labelled probe. The absorbance was measured after 20 minutes incubation with the 3'FADP-based enzyme amplification assay.

The amount of conjugate hybridized to the microtitre plate was quantitated using the amplification assay described in Example 2. FIG. 5 shows that as little as 35 amol of DNA can be detected in this way in a total assay time of 90 minutes (10 minutes denaturation, 60 minutes hybridization and 20 minutes of amplification assay).

It will be seen that the enzyme labels used in preferred embodiments of the present invention are smaller, more stable, less prone to non-specific binding, and give less background from endogenous phosphatases than those previously described.

The above description contains many specificities which should not be construed as limitations on the scope of the invention, but rather as exemplifications of preferred embodiments thereof. Many other variations are possible. For example, apo-D-amino oxidase could be used instead of apo-glucose oxidase, as the apoenzyme.

What is claimed is:

1. A probe for use in an enzyme-linked assay comprising (1) a disulfide-activated nuclease enzyme selected from active P1 and active S1 nucleases and (2) a specific binding member ("sbm") selected from an antibody, or a functional fragment thereof, and a single-stranded nucleic acid, the single-stranded nucleic acid having a 5'-end bearing a thiol group, the enzyme and the sbm being covalently attached to each other via a disulfide exchange linkage.

2. The probe of claim 1 wherein the nuclease enzyme is a 2-pyridyl disulphide-activated nuclease enzyme.

3. An enzyme-linked assay employing the probe of claim 2 comprising the steps of:
   (i) contacting a sample suspected of containing an analyte with a carrier having a carrier sbm immobilized to it, wherein the analyte in the sample binds to the carrier sbm;
   (ii) contacting the sample with the probe of claim 2 wherein the probe binds to the analyte via the probe sbm; and
   (iii) contacting the bound probe with a substrate, wherein activity of the nuclease on the substrate leads to a detectable signal.

4. An assay according to claim 3 wherein the probe sbm comprises antihuman IgG antibody, the carrier sbm comprises measles antigen, and the analyte comprises human serum IgG antibodies to measles.

5. An assay according to claim 3 wherein the probe comprises an oligonucleotide and the analyte comprises single-stranded DNA.

6. An assay according to claim 3 wherein the substrate comprises an apoenzyme which is converted into a holoenzyme by interaction with an accessory subunit; and a masked form of said subunit which is converted into its active unmasked form by the action of the nuclease of the probe.

7. An assay according to claim 6 wherein said subunit is FAD and said masked form is 3'-FADP.

8. An assay according to claim 6 wherein said apoenzyme is apo-glucose oxidase or apo-D-amino oxidase.

9. An enzyme-linked assay employing the probe of claim 1 comprising the steps of:
   (i) contacting a sample suspected of containing an analyte with a carrier having a carrier sbm immobilized to it wherein the analyte in the sample binds to the carrier sbm;
   (ii) contacting the sample with the probe of claim 1 wherein the probe binds to the analyte via the probe sbm; and
   (iii) contacting the sample containing the bound probe with a substrate comprising apo-glucose oxidase or apo-D-amino oxidase and 3'-FADP, wherein 3' FADP is converted to FAD by the action of the nuclease to produce a detectable signal.

10. An assay kit comprising:
    (1) a probe composed of a disulfide-activated nuclease enzyme selected from active P1 and active S1 nucleases covalently attached to a specific binding member ("sbm") selected from an antibody, or a functional fragment thereof, and a single-stranded nucleic acid, the single-stranded nucleic acid having a 5'-end bearing a thiol group and the covalent attachment of the enzyme to the sbm being through a disulfide exchange linkage;
    (2) a 3'-FADP capable of being hydrolyzed by a nuclease P1 or S1 enzyme to yield FAD;
    (3) an apoenzyme capable of forming a holoenzyme with FAD, the apoenzyme being selected from apo-glucose oxidase and apo-D-amino oxidase; and
    (4) a substrate capable of reacting with the holoenzyme to generate a detectable signal.

* * * * *

SEQUENCE LISTING (1) GENERAL INFORMATION:

(iii) NUMBER OF SEQUENCES: 2

(2) INFORMATION FOR SEQ ID NO: 1

-continued

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 1

GAATTCCCAT GGCGAAGGAA TCCGCTGCCG CTAAA                               35

(2) INFORMATION FOR SEQ ID NO: 2

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 2

GGTCACCTGC GAAAACGGGC AGG                                            23
```